(12) United States Patent
Petrov et al.

(10) Patent No.: US 7,034,297 B2
(45) Date of Patent: Apr. 25, 2006

(54) METHOD AND SYSTEM FOR USE IN THE MONITORING OF SAMPLES WITH A CHARGED PARTICLE BEAM

(75) Inventors: Igor Petrov, Holon (IL); Zvika Rosenberg, Mevasseret Zion (IL); Pavel Adamec, Haar (DE); Igor Krayvitz, Rehovot (IL)

(73) Assignee: Applied Materials, Israel, Ltd., Rehovot (IL)

( * ) Notice: Subject to any disclaimer, the term of this patent is extended or adjusted under 35 U.S.C. 154(b) by 96 days.

(21) Appl. No.: 10/382,789

(22) Filed: Mar. 5, 2003

(65) Prior Publication Data

US 2004/0173746 A1    Sep. 9, 2004

(51) Int. Cl.
G21G 5/00 (2006.01)
G01R 31/28 (2006.01)
H01J 37/28 (2006.01)
H01J 37/26 (2006.01)

(52) U.S. Cl. ............ 250/310; 250/306; 250/307; 250/309; 250/396 R; 250/396 ML; 250/397; 250/398; 250/492.1; 250/492.2; 250/492.21; 250/492.3

(58) Field of Classification Search ........... 250/310, 250/397, 492.2–492.3, 492.1
See application file for complete search history.

(56) References Cited

U.S. PATENT DOCUMENTS

| | | | |
|---|---|---|---|
| 4,831,266 A * | 5/1989 | Frosien et al. ............ | 250/397 |
| 5,051,556 A * | 9/1991 | Sakamoto et al. ......... | 219/121.25 |
| 5,194,741 A * | 3/1993 | Sakamoto et al. ......... | 250/492.2 |
| 5,329,125 A | 7/1994 | Feuerbaum | |
| 5,689,117 A * | 11/1997 | Nakasuji ............... | 250/492.23 |
| 5,734,164 A | 3/1998 | Sanford | |
| 5,747,819 A * | 5/1998 | Nakasuji et al. ........ | 250/492.23 |
| 5,770,863 A * | 6/1998 | Nakasuji ............... | 250/492.2 |
| 5,847,402 A * | 12/1998 | Nakasuji ............... | 250/492.2 |
| 5,894,124 A | 4/1999 | Iwabuchi et al. | |
| 6,037,589 A | 3/2000 | Yonezawa et al. | |
| 6,218,664 B1 * | 4/2001 | Krans et al. ............ | 250/310 |
| 6,232,787 B1 * | 5/2001 | Lo et al. ................ | 324/751 |
| 6,274,876 B1 * | 8/2001 | Kawanami et al. ....... | 250/492.22 |
| 6,380,546 B1 | 4/2002 | Petrov et al. | |
| 6,504,164 B1 * | 1/2003 | Yonezawa et al. ....... | 250/492.3 |
| 6,630,681 B1 * | 10/2003 | Kojima ............... | 250/492.22 |
| 6,664,552 B1 * | 12/2003 | Shichi et al. ............ | 250/492.21 |
| 6,717,145 B1 * | 4/2004 | Takagi et al. ............ | 250/311 |
| 2002/0079463 A1 * | 6/2002 | Shichi et al. ............ | 250/492.1 |

FOREIGN PATENT DOCUMENTS

| | | |
|---|---|---|
| EP | 1 045 425 A2 | 10/2000 |
| EP | 1 045 425 A3 | 3/2003 |
| WO | WO 01/05056 A1 | 6/2000 |
| WO | WO 01/45136 A1 | 6/2001 |

* cited by examiner

Primary Examiner—John R. Lee
Assistant Examiner—Bernard E. Souw
(74) Attorney, Agent, or Firm—Tarek N. Fahmi

(57) ABSTRACT

A method and apparatus for use in monitoring a sample with a charged particle beam are presented. A mechanical displacement between a plane defined by the sample's surface and an optical axis defined by a beam directing arrangement is provided so as to orient the sample at a certain non-right angle $\theta_1$ with respect to the optical axis. A primary charged particle beam propagating towards the sample is deflected so as to affect the trajectory of the primary charged particle beam to provide a certain non-zero angle $\theta_2$ between the primary beam propagation axis and said optical axis.

32 Claims, 6 Drawing Sheets

METHOD AND SYSTEM FOR USE IN THE MONITORING OF SAMPLES WITH A CHARGED PARTICLE BEAM

FIELD OF THE INVENTION

This invention is in the field of monitoring techniques of the kind utilizing irradiation of a sample by a focused beam of electrically charged particles, such as electrons, positrons, or ions, and relates to a method and apparatus for optimizing the charged particle beam incidence onto a sample.

BACKGROUND OF THE INVENTION

Charged particle beam columns are typically employed in scanning electron microscopy (SEM), which is a known technique widely used in the manufacture of semiconductor devices, being utilized in a CD metrology tool, the so-called CD-SEM (critical dimension scanning electron microscope) and defect review SEM. In an SEM, the region of a sample to be examined is two-dimensionally scanned by means of a focused primary beam of electrically charged particles, usually electrons. Irradiation of the sample with the primary electron beam releases secondary (and/or backscattered) electrons. The secondary electrons are released at that side of the sample at which the primary electron beam is incident, and move back to be captured by a detector, which generates an output electric signal proportional to the so-detected electric current. The energy and/or the energy distribution of the secondary electrons is indicative of the nature and composition of the sample.

SEM typically includes such main constructional parts as an electron beam source (formed with a small tip called "electron gun"), an electron beam column and a detector unit. The electron beam column comprises inter alia a beam aligning means, a beam shaping means, and a beam directing arrangement that includes a lens arrangement and a deflection system for directing a primary electron beam onto a sample and directing secondary electrons towards one or more detection units.

Some systems of the kind specified utilize an objective lens arrangement in the form of a combination of a magnetic objective lens and an electrostatic lens, the so-called "compound magnetic-electrostatic lens" (e.g., WO 01/45136 and EP 1045425, both assigned to the assignee of the present application, and WO 01/5056). The electrostatic part of the compound magnetic-electrostatic lens is an electrostatic lens having two electrodes held at different potentials, one electrode being formed by a cylindrical anode tube which is arranged within a magnetic objective lens along its optical axis, and the other electrode being a metallic cup provided below the magnetic objective lens.

A need for a retarding field is associated with the following. On the one hand, in order to reduce the "spot" size of the electron beam up to nanometers, a highly accelerated electron beam is typically produced using accelerating voltages of several tens of kilovolts and more. Specifically, the electron optic elements are more effective (i.e., produce smaller aberrations) when the primary electrons are accelerated to high kinetic energy. Hence, the primary electrons are accelerated on their way towards the magnetic objective lens. On the one hand, such a highly energized primary electron beam causes damage to resist structures and integrated circuits, and, in the case of dialectical samples, causes the undesirable charging of the sample. To avoid these effects and to also facilitate the extraction of secondary charged particles from the sample, a retarding field (with respect to primary electrons) is created in the vicinity of the sample.

Inspection and/or measurement on patterned surfaces, especially for CD measurements, might require an operation with the so-called "tilt mode", at which a primary electron beam impinges onto a sample with a certain non-zero angle of incidence. It is known to implement a tilt mechanism by mechanically tilting the sample's carrier with respect to the charged particle beam column, tilting the column with respect to the sample's carrier, or both of them (e.g., U.S. Pat. Nos. 5,329,125; 5,734,164; 5,894,124; 6,037,589). It is also known to achieve a tilt mechanism by affecting the trajectory of the primary electron beam using single- or double-deflection (e.g., WO 01/45136 and U.S. Pat. No. 6,380,546 assigned to the assignee of the present application).

SUMMARY OF THE INVENTION

There is a need in the art to facilitate the monitoring of samples by a charged particle beam, by providing a novel method and apparatus aimed at optimizing the charged particle beam incidence onto a sample, and/or the detection of a secondary charged particle beam.

The term "primary beam" used herein (being also referred to as "primary charged particle beam" or "primary electron beam") signifies a charged particle beam, which is formed by charged particles generated by a source (cathode) of these particles, and which is to be directed to a sample to knock out charged particles forming a "secondary beam" (also referred to as "secondary charged particle beam or secondary electron beam"), which is to be detected. The term "monitoring" used herein signifies at least one of the inspection and measurement techniques.

The present invention provides for combining the so-called "mechanical tilt" of a sample with respect to a charged particle beam column and "electronic tilt" of a primary charged particle beam propagating towards the sample, to thereby provide a desirably high angle of incidence of the primary beam at as large as possible image resolution and as low as possible power. This technique also provides for improved detection of secondary charged particles.

The term "mechanical tilt" signifies mechanically inclining either one of the sample carrier and a charged particle beam column with respect to the other, or both of them, and the term "electronic tilt" signifies affecting the trajectory of the primary beam propagation through the charged particle beam column.

The inventors have found that using either the purely electronic tilt or the purely mechanical tilt to provide a desired angle of incidence (larger than 10°, e.g., in the range of 10°–25°) while meeting the requirements to the image resolution and power, deteriorates the system operation performances.

More specifically, the use of the purely mechanical tilt impedes the collection of the secondary charged particles, especially when operating with the HAR mode and/or when using the so-called "in-lens or in-column" detector. The in-column detector is formed with an opening surrounded by sensing regions of the detector, and is accommodated in the path of a primary beam such that the primary beam propagation axis intersects with said opening, which therefore serves as the primary beam hole. The HAR mode consists of creating a high-gradient electric field in the vicinity of a sample resulting in that secondary charged particles are relatively fast accelerated and propagate from the sample along an axis perpendicular to the sample's surface. The experiments have shown that, when operating with the HAR mode and purely mechanical tilt of about 8°–10° and more (angle between the sample's carrier and a horizontal plane), at least a part of the secondary charged particles hits the funnel (the inner walls of the anode tube). Using a higher diameter funnel unavoidably needs higher diameter pole pieces of the magnetic objective lens, which increases the power supply to the deflecting elements of the beam directing arrangements resulting in the image drift.

The use of the mechanical tilt results in the creation of a non-flat electrostatic field between the electrode closest to the sample's surface (e.g., the "cup electrode" of an electrostatic lens) and the tilted sample. This electrostatic field affects the trajectory of a primary beam to deflect it away form the optical axis in a direction of the mechanical tilt. Since the effective primary beam incidence onto the sample is determined by the sum of the mechanical tilt and any electronic tilt caused by the electric field in the vicinity of the sample, the use of the purely mechanical tilt increases the effective tilt angle.

Another important parameter in the inspection of samples with a charged particle beam column is the so-called working distance. The term "working distance" is typically referred to as the distance between the sample's plane and the electrode of the lens arrangement closest to the sample's plane (usually the cup electrode of the electrostatic lens). The working distance should be as small as possible, and the minimal possible working distance is typically defined by an arcing problem. Keeping in mind that CD-measurements typically require the cup electrode perpendicular to the optical axis of the lens arrangement (flat electrostatic field) and the physical dimensions of this electrode, the mechanical tilt will unavoidably increase the working distance. For example, a 10° mechanical tilt (angle between the sample's carrier and a horizontal plane) results in the working distance increasing from 0.8 mm to 2 mm. Accordingly, in order to achieve the same electrostatic field needed for decelerating the primary and accelerating the secondary electrons, a higher potential is to be applied to the cup electrode, thereby causing the image shift.

The use of the purely electronic tilt to achieve a desirably high angle of primary beam incidence results in an image draft and reduction in the collection efficiency of secondary charged particles. The image drift is provoked by a thermal effect caused by high electrical currents through the beam shift coils (e.g., about 7A at 15° tilt). The secondary particles' collection is reduced as the secondary particles become propagating towards the inner walls of an anode tube. Moreover, the electronic tilt of angles higher than 10° increases the coma aberrations.

The present invention solves the above problems by utilizing a combination of the mechanical and electronic tilts. The technique of the present invention provides for the achievement of a desirably large angle of primary beam incidence (i.e., desirable high combined tilt, preferably 10° and higher) with the full collection of secondary charged particles and better resolution than that obtained with either a mechanical or electronic tilt separately. Here, the term "effective tilt" or "combined tilt" signifies the primary beam angle of incidence, namely, the angle between an axis, at which the primary beam impinges onto the sample, and the normal to the sample. The technique of the present invention is based on the fact that the mechanical tilt practically does not affect the image resolution, while the electronic tilt of less angles results in less coma aberrations.

Thus, according to one aspect of the present invention, there is provided a method for use in monitoring a sample with a charged particle beam, the method comprising:
providing a mechanical displacement between a plane defined by the sample's surface and an optical axis defined by a beam directing arrangement of a charged particle beam column, so as to orient the sample with a certain non-right angle $\theta_1$ with respect to the optical axis;
deflecting the primary charged particle beam propagating towards the sample to affect the trajectory of the primary charged particle beam to thereby form a certain non-zero angle $\theta_2$ between the primary beam propagation axis and said optical axis.

The non-right angle $\theta_1$ between the plane defined by the sample's surface and the optical axis can be provided by displacing either one of the sample's carrier and the beam directing arrangement (or the entire charged particle beam column), or both the sample's carrier and the beam directing arrangement. The trajectory of the primary particle beam is affected by one or more deflection field in the primary beam path. If a single deflection field is used, it is provided within the magnetic lens gap (i.e., between the pole pieces of an objective lens). In this case, the deflection field deflects the primary beam away from the optical axis, and an electric field, created by the lens arrangement in the vicinity of the sample, further affects the trajectory of the beam. Preferably, at least two deflection fields are provided at two successive regions, respectively, of the primary beam path. The first deflection field deflects the primary beam propagation axis away from the optical axis, and the second deflection field deflects the so-deflected primary beam propagation axis towards the optical axis, so as to provide either an on-axis tilt (a location of interaction between the primary beam and the sample's surface lies on the optical axis) or an off-axis tilt. The angles $\theta_1$ and $\theta_2$ may and may not be equal to one another.

The deflecting of the primary beam is needed to provide a desired incidence of the primary beam onto the sample, namely, oblique incidence ("tilt mode"), or selective switching between the oblique incidence and normal incidence ("normal mode"), at which the primary beam impinges onto the sample along an axis substantially perpendicular to the sample's surface. The need for deflecting the secondary beam is associated with the need for separating between the primary and secondary beams' paths, especially when utilizing the "in-column" or "in-lens" detector, to thereby prevent the secondary electrons' loss in the opening of the detector (the so-called "primary beam hole").

According to another broad aspect of the present invention, there is provided a method for use in monitoring a sample with a charged particle beam, the method comprising irradiating the sample with a primary charged particle impinging onto the sample with a desired angle of incidence, said irradiating with the desired angle of incidence comprising:
providing a mechanical displacement between a plane defined by the sample's surface and an optical axis defined by a beam directing arrangement of a charged particle beam column, so as to orient the sample with a certain non-right angle $\theta_1$ with respect to the optical axis;
deflecting the primary charged particle beam propagating towards the sample to affect the trajectory of the primary charged particle beam to thereby form a certain non-zero angle $\theta_2$ between the primary beam propagation axis and said optical axis.

According to yet another aspect of the invention, there is provided a method for use in monitoring a sample with a charged particle beam, the method comprising controlling detection of secondary charged particles resulting from interaction of a primary charged particle beam with the sample, said controlling comprising:

provproviding a mechanical displacement between a plane defined by the sample's surface and an optical axis defined by a beam directing arrangement of a charged particle beam column, so as to orient the sample with a certain non-right angle $\theta_1$ with respect to the optical axis;

creating at least first and second deflection fields to sequentially affect the trajectory of the primary charged particle beam to thereby direct the primary charged particle beam onto the sample's surface with a certain non-zero angle $\theta_2$ between the primary beam propagation axis and said optical axis, and to affect the trajectory of the secondary charged particle beam to direct the secondary charged particle beam from the sample along a path different from that of the primary charged particle beam;

the method thereby enabling detection of substantially the entire secondary charged particles.

The first and second deflection fields may be created by first and second deflectors, respectively, or by a deflector and an electric field created by a lens arrangement in the vicinity of the sample.

According to yet another aspect of the present invention, there is provided an apparatus for use in monitoring a sample by a charged particle beam, the apparatus comprising:

a beam directing arrangement having a deflector arrangement operable to affect the trajectory of a primary charged particle beam to direct it towards the sample's surface with a certain non-zero angle $\theta_2$ between the primary beam propagation axis and an optical axis of the beam directing arrangement, and affecting the trajectory of a secondary charged particle beam, resulting from interaction of the primary charged particle beam with the sample, to direct the secondary charged particle beam from the sample along a path different from that of the primary charged particle beam;

a stage for handling the sample under inspection;

a drive assembly operable to provide a relative mechanical displacement between the stage and the beam directing arrangement to orient the stage at a certain non-right angle $\theta_1$ with respect to the optical axis; and a control unit operating a power supply to said beam deflector arrangement and operating said drive assembly to provide the desired values of said angles $\theta_1$ and $\theta_2$.

The present invention according to its yet another broad aspect provides an apparatus for use in monitoring a sample by a charged particle beam, the apparatus comprising:

a beam directing arrangement having a deflector arrangement operable to affect the trajectory of a primary charged particle beam to direct the primary charged particle beam towards the sample's surface with a certain non-zero angle $\theta_2$ between the primary beam propagation axis and an optical axis of the beam directing arrangement, and to affect the trajectory of a secondary charged particle beam, resulting from interaction of the primary charged particle beam with the sample, to direct the secondary charged particle beam from the sample along a path different from that of the primary charged particle beam;

a detection unit having a detector, that has an opening and sensing regions outside said opening for sensing the secondary charged particles, and is oriented with respect to the optical axis such that said optical axis passes through said opening, thereby enabling the primary charged particles beam passage towards the sample through said opening;

a stage for handling the sample under inspection;

a drive assembly operable to provide a relative mechanical displacement between the stage and the beam directing arrangement to thereby orient the stage at a certain non-right angle $\theta_1$ with respect to the optical axis; and a control unit operating a power supply to said beam deflector arrangement and operating said drive assembly to provide the desired values of said angles $\theta_1$ and $\theta_2$.

According to yet another aspect of the invention, there is provided an apparatus for use in monitoring a sample by a charged particle beam, the apparatus comprising:

a means for producing a primary charged particle beam and directing it towards a sample, to thereby cause interaction of the primary charged particle beam with the sample resulting in a secondary charged particle beam propagation from the sample;

a means for focusing the primary charged particle beam onto a scan area of the sample;

a beam deflecting means operable to affect the trajectory of the primary charged particle beam while being focused onto the sample so as to provide the primary charged particle beam incidence onto the scan area along an axis forming a certain non-zero angle $\theta_2$ with an optical axis of a focusing means, and to affect the trajectory of the secondary charged particle beam to direct the secondary charged particle beam along a path different from that of the primary charged particle beam;

a means for handling the sample on a substantially flat surface;

a driving means operable to provide a relative mechanical displacement between said flat surface and the focusing means to thereby orient said surface at a certain non-right angle $\theta_1$ with respect to the optical axis; and a control means for operating said deflecting means and operating said driving means to provide the desired values of said angles $\theta_1$ and $\theta_2$.

According to yet another broad aspect of the invention, there is provided an apparatus for use in monitoring a sample by a charged particle beam, the apparatus comprising:

a charged particle beam column having a beam focusing arrangement defining an optical axis, and having a beam deflector arrangement operable to affect the trajectory of a primary charged particle beam to focus it onto the sample's surface with a certain non-zero angle $\theta_2$ between the primary beam propagation axis and said optical axis, and to affect the trajectory of a secondary charged particle beam, resulting from interaction of the primary charged particle beam with the sample, to direct the secondary charged particle beam from the sample along a path different from that of the primary charged particle beam;

a stage for handling the sample under inspection;

a drive assembly operable to provide a relative mechanical displacement between the stage and the charged particle beam column to thereby create a certain non-right angle $\theta_1$ between the optical axis and a plane defined by the stage; and a control unit operating a power supply to said beam deflector arrangement and operating said drive assembly to provide the desired values of said angles $\theta_1$ and $\theta_2$.

The beam directing arrangement comprises a lens arrangement and a deflector arrangement. The lens arrangement is designed to create a focusing field in the optical path of the primary beam, wherein the focusing field preferably also acts as a retarding field with respect to the primary charged particle beam in the vicinity of the sample's surface, and as accelerating field with respect to secondary charged particles. The lens arrangement comprises an objective magnetic lens, and preferably also comprises an electrostatic lens, which whilst decelerating the electrons of the primary beam, acts as an accelerating field for the secondary electrons. The provision of a retarding field, as well as any electrostatic lens as an actual physical element, is optional. If deceleration of the primary electrons is required, this effect can be achieved by applying appropriate voltages to the anode tube and the sample, or to the anode tube, polepiece of the objective lens and sample.

The deflector arrangement comprises one or more deflector units located in the path of the charged particle beam. The deflectors may be arranged in the so-called "in-lens", "pre-lens", "post-lens" or combination thereof fashion, considering the deflector's locations relative to the objective lens. A beam-shift deflector, typically provided within the magnetic lens gap defined by the polepieces of the objective lens and used for scanning purposes, can be used as the in-lens deflector. The advantageous use of double deflection by means of in-lens and post-lens deflectors for both scanning and tilt purposes is disclosed in U.S. Pat. No. 6,380,546, assigned to the assignee of the present application.

It should be understood that the present invention can be used in a charged particle beam column of any kind, namely, a column for directing a primary charged particle beam formed by electrons, positrons, or ions towards a scan area of a sample. More specifically, the present invention is used with an electron beam column (such as used in SEM), and is therefore described below with respect to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
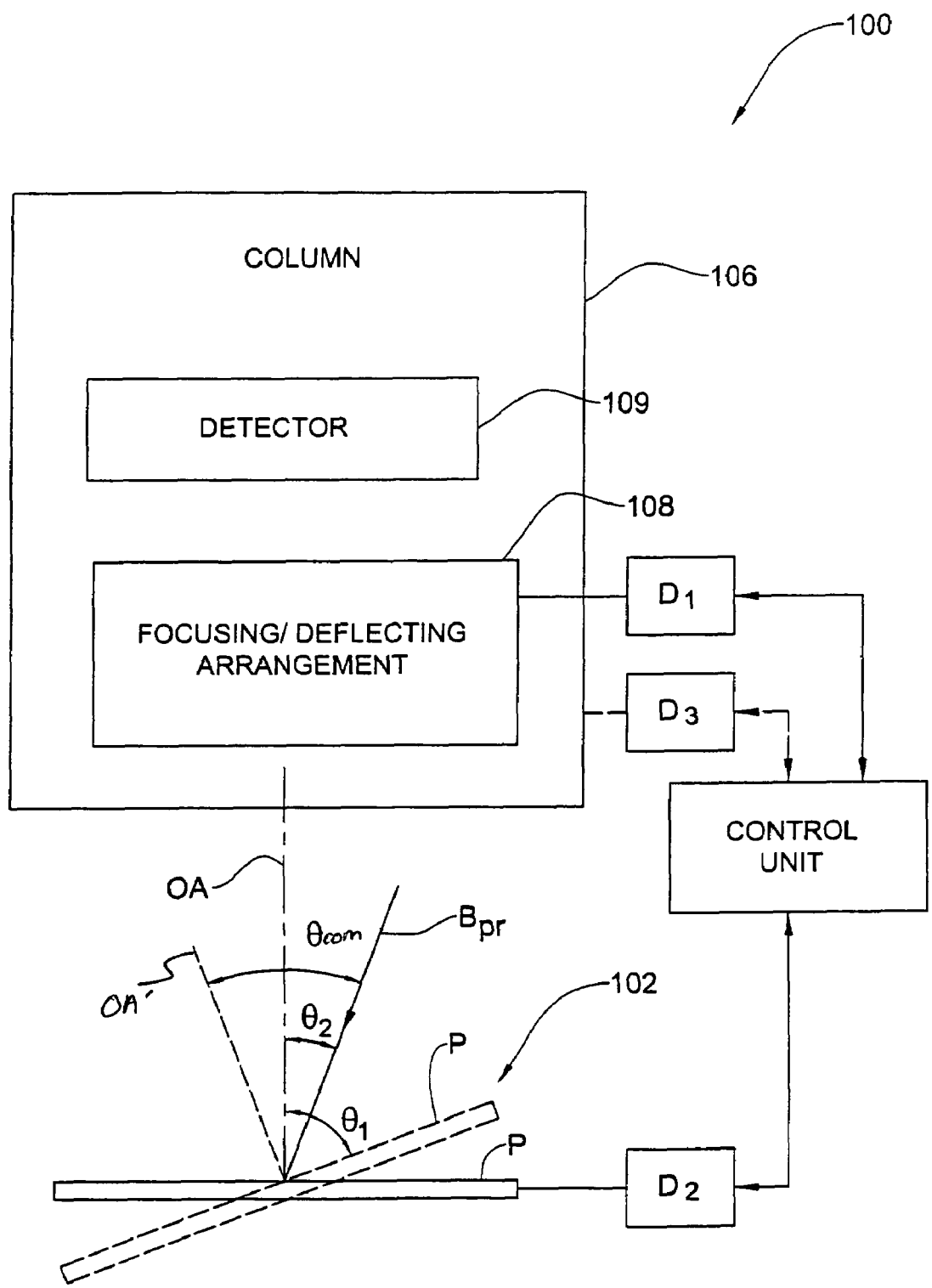
FIG. 1 is a schematic block diagram of a monitoring apparatus according to the present invention.

Referring to FIG. 1, there is illustrated, by way of a block diagram, the main components of a monitoring apparatus 100 according to the invention. The apparatus 100 comprises a stage 102 for handling a sample; a charged particle beam column 106 including inter alia a beam directing arrangement 108 including a lens arrangement and a deflector arrangement that is associated with a power supply unit $D_1$ for driving electric currents to one or more deflectors; a detector 109 which in the present example is an in-column detector; a drive assembly which includes a drive mechanism $D_2$ associated with the stage and/or a drive mechanism $D_3$ associated with the column 106 (or at least the beam directing arrangement therein); and a control unit CU connectable to the power supply unit $D_1$ and to the drive assembly. The control unit CU operates the drive assembly to provide a certain non-right angle $\theta_1$ between a plane P defined by the stage and an optical axis OA of the beam directing arrangement (for example by inclining the stage only), and operates the power supply unit to effect deflection of a primary electron beam $B_{pr}$ so as to provide its incidence onto the sample's surface along an axis OA' forming a certain non-zero angle $\theta_2$ with the optical axis OA. The primary beam incident angle (the so-called "combined tilt angle") $\theta_{com}$ is defined by the angles $\theta_1$ and $\theta_2$, i.e., $\theta_{com}=90-\theta_1+\theta_2$.

FIGS. 2A–2D illustrate four examples, respectively, of the implementation of the monitoring apparatus 100. In all these examples, a relative mechanical displacement between the sample carrying stage 102 and the beam directing arrangement to create a certain non-right angle $\theta_1$ between the stage and the optical axis OA, is provided by tilting 25 the stage 102 with respect to the optical axis OA. It should, however, be understood that the same can be achieved by displacing the column (or at least the beam directing arrangement thereof) or both the column and the stage. The beam directing arrangement comprises a lens arrangement 110 and a deflector arrangement 118. The lens arrangement includes an objective lens that is typically a magnetic lens formed by coils and two pole pieces 112A and 112B; and an electrostatic lens formed by three electrodes—electrode 114A constituted by the lower end of an anode tube 115, electrode 114B constituted by the sample's surface, and electrode 114C (cup electrode) located between the electrodes 114A and 114B.

The electrostatic lens serves for regulating an electric field created within the vicinity of the sample to decelerate primary electrons in the closest vicinity of the sample and accelerate secondary electrons knocked out from the sample. When using such a three-electrode electrostatic lens, the retarding field is created by applying voltage to the electrode 114B substantially less than that applied to the electrode 114A. For example, the sample is grounded ($V_{114B}=0$), and the electrodes are biased, that is the following voltages may be applied to, respectively, cathode (not shown), anode tube 115 and cup-electrode 114C: (−1)kV; (+8)kV and (+3)kV. The electric field produced by the electrostatic lens 114, whilst decelerating the electrons of the primary beam, acts as an accelerating field for the secondary electrons.

A need for a retarding field is associated with the following. On the one hand, in order to reduce the "spot" size of the electron beam up to nanometers, a highly accelerated electron beam is typically produced using accelerating voltages of several tens of kilovolts and more. Specifically, the electron optic elements are more effective (i.e., produce smaller aberrations) when the primary electrons are accelerated to high kinetic energy. Hence, the primary electrons are accelerated on their way towards the magnetic objective lens. On the one hand, such a highly energized primary electron beam causes damage to resist structures and integrated circuits, and, in the case of dialectical samples, causes the undesirable charging of the sample. To avoid these effects, and also to facilitate the extraction of secondary charged particles from the sample, a retarding field (with respect to the primary electrons) is created in the vicinity of the sample.

It should be noted that the provision of a retarding field, as well as any electrostatic lens as an actual physical element, is optional. If deceleration of the primary electrons is required, this effect can be achieved by applying appropriate voltages to the anode tube and sample, or to the anode tube, polepiece of the objective lens and sample. The following are two possible examples of the electric parameters: (1) the sample is biased to (−5)kV, the anode voltage is equal to zero and the cathode voltage is (−6)k; and (2) the sample is biased to (−3)kV, the polepiece voltage is equal to zero, and the anode and cathode voltage are, respectively, (+5)kV and (−4)kV.

Figure 2A:
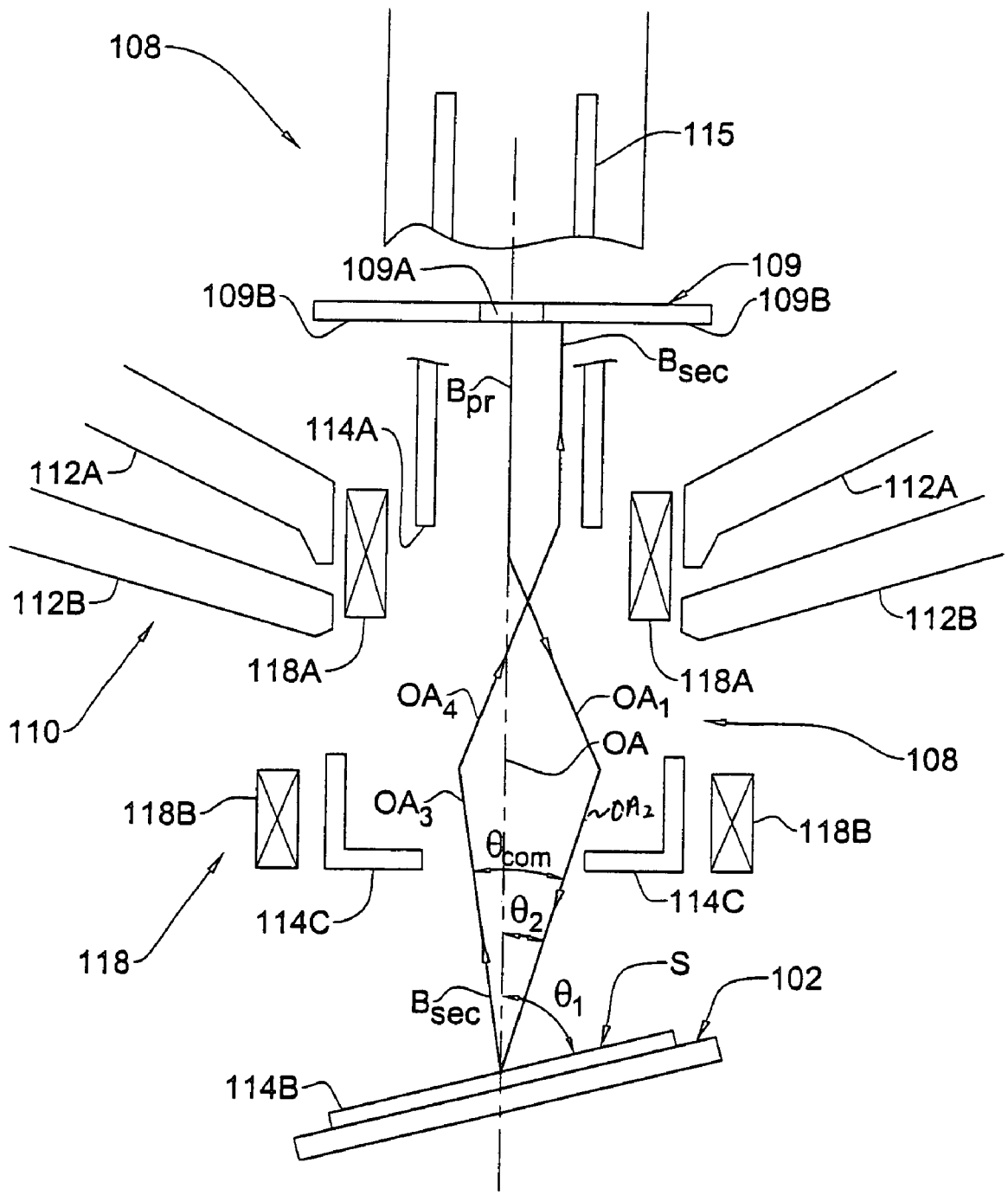
FIGS. 2A–2D illustrate four examples, respectively, of the implementation of the monitoring apparatus of FIG. 1.
Figure 2B:
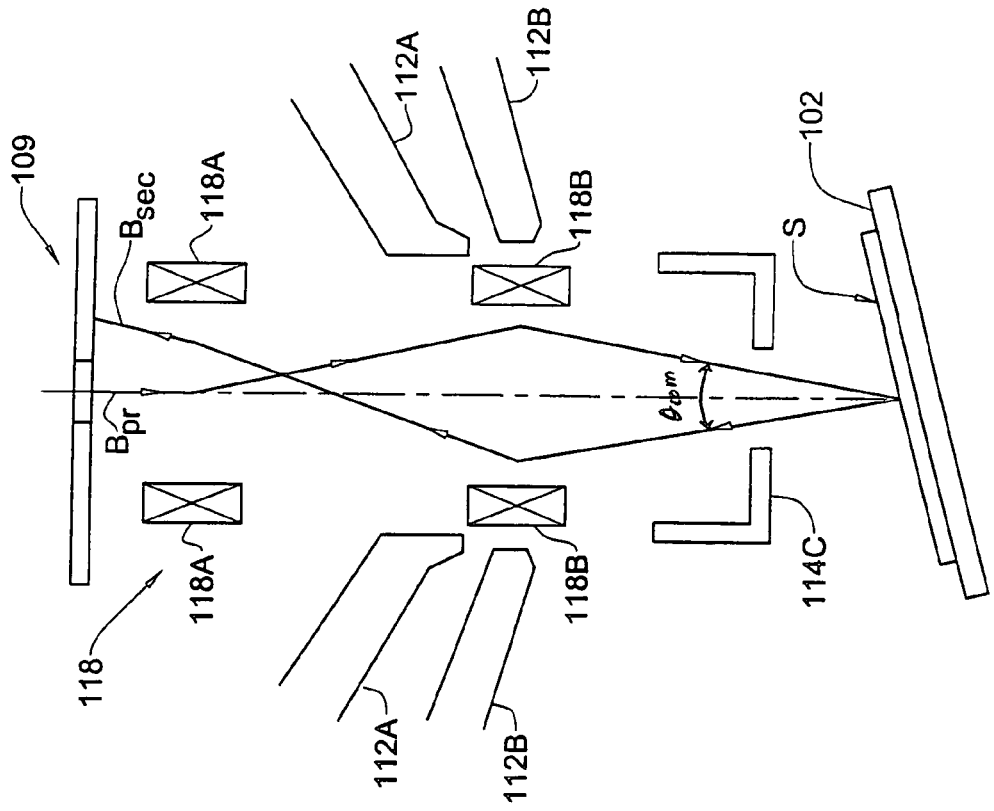
Figure 2C:
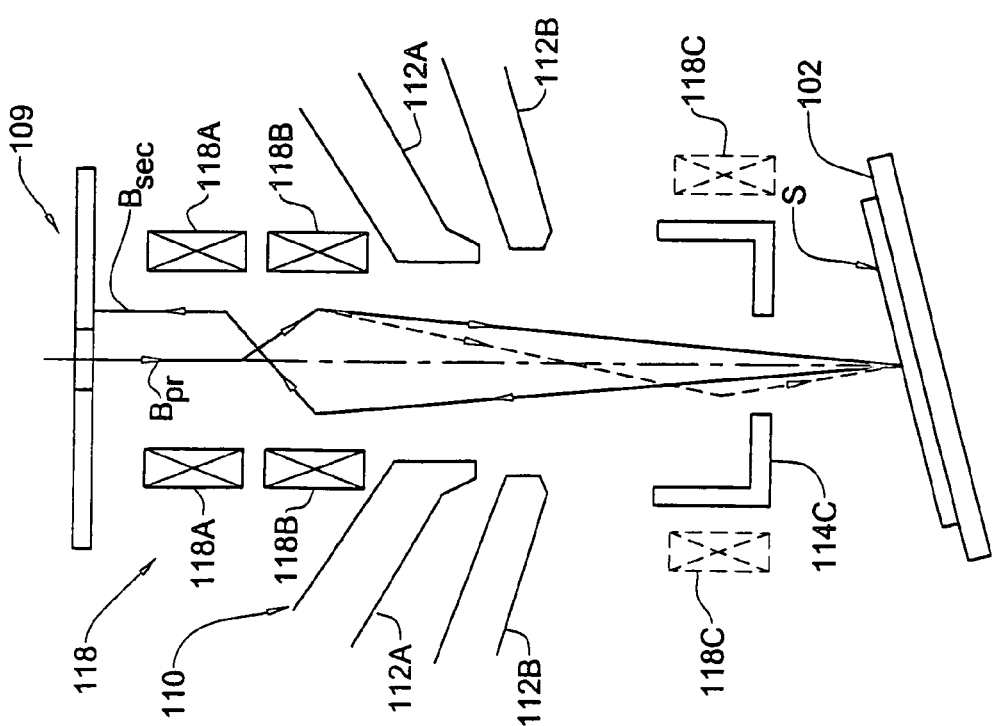

In the examples of FIGS. 2A–2C, the deflector arrangement 118 includes two deflectors 118A and 118B, and the HAR mode of system operation is illustrated (e.g., $V_{cup}$=3 kV). These examples differ from each other in the accommodation of the deflectors 118A and 118B with respect to the objective lens 112. In the example of FIG. 2A, the deflectors 118A and 118B are, respectively, in-lens and post-lens deflectors. The in-lens deflector 118A may be a beam-shift deflector typically provided in the magnetic lens gap (in a space between the pole pieces 112A and 112B) or an additional deflector located adjacent to the beam-shift deflector. The post-lens deflector 118B is located closer to the sample's surface (e.g., adjacent to the cup-electrode 114C). It should be understood that the terms "in-lens" and "post-lens" correspond to the deflectors' locations relative to the pole pieces of the objective lens 1129 while both deflectors are located within the focusing field of the entire lens arrangement 110. The first deflector 118A is a magnetic deflector, and the second deflector 118B may be either magnetic (as in the present example), or electrostatic (e.g., in the form of condenser plates). In the example of FIG. 2B, the deflectors 118A and 118B are, respectively, pre-lens and in-lens deflectors. In the example of FIG. 2C, the deflectors 118A and 118B are both pre-lens deflectors. It should be noted, although not specifically shown that, generally, more than two deflectors can be used for the purposes of the present invention, namely, to provide the primary beam incidence into the sample's surface along an axis forming a certain angle with the optical axis OA defined by the lens arrangement.

The deflectors 118A and 118B operate together to affect the trajectory of the primary beam $B_{pr}$ so as to provide the desired incidence of the focused primary beam onto the sample, and to affect the trajectory of the secondary beam $B_{sec}$ to facilitate its detection by the detector 109. As shown, the primary beam $B_{pr}$ enters the beam directing arrangement along an axis substantially parallel to the optical axis OA. The first upper deflector 118A deflects the primary beam $B_{pr}$ away from the optical axis to propagate along an axis $OA_1$ forming a certain angle (e.g., about 1°–3°) with the optical axis OA. The second lower deflector 118B then appropriately deflects the primary beam $B_{pr}$ towards the optical axis OA to propagate along an axis $OA_2$ forming an angle $\theta_2$ (e.g., about 10°) with the optical axis OA. Thus, the primary beam $B_{pr}$ while being focused onto the sample by the lens arrangement is affected by the deflector arrangement to impinge onto the sample with a certain incident angle $\theta_{com}$ defined by the angles $\theta_1$ and $\theta_2$.

In these examples, the so-called "on-axis" electronic tilt is illustrated. It should, however, be understood that the deflectors can operate to provide the primary beam incidence onto the sample at a location spaced-apart from the optical axis OA (the so-called "off-axis" tilt). When using the double pre-lens deflection, the deflectors' operation is controlled to ensure the primary beam passage through a specific point of the objective lens arrangement, usually called the "central" point thereof. This "specific point" is such that changing the energy of a beam that passes through this point in the objective lens arrangement will not cause the beam deflection by the objective lens arrangement, to thereby ensure minimal spot-size imaging of the cathode-tip onto the sample's surface.

In this case, in order to provide a desired incidence of the primary beam onto the sample, an additional post-lens deflector 118C (shown in dashed lines), as illustrated in FIG. 2C, is preferably used to further deflect the beam $B_{pr}$ towards the optical axis.

With regard to the secondary beam propagation, the following should be understood. If no voltage is supplied to the cup-electrode of the electrostatic lens ($V_{cup}$=0), the electrostatic lens creates a low gradient electric field in the vicinity of the sample, and thus acts as a short-focus lens for the secondary electrons. The latter therefore cross over the optical axis in the vicinity of the sample, and become directed to regions of the detector at opposite sides of the primary beam hole. When operating with the HAR mode, which is typically the case (e.g., $V_{cup}$ is about 3 kV), a high-gradient electric field is created in the vicinity of the sample, and the secondary electrons $B_{sec}$ are thus relatively fast accelerated and define a less cross section of the secondary beam (as compared to the operational mode with $V_{cup}$=0. The secondary beam $B_{sec}$ thus propagate from the sample's surface along an axis $OA_3$ perpendicular to the sample's surface, and, upon reaching the deflection field of the lower deflector 118B, becomes deflected to propagate along an axis $OA_4$ towards the deflection field of the upper deflector 118A, which further deflects the beam $B_{sec}$ in opposite direction to propagate along an axis $OA_5$. To achieve the required deflection fields, the control unit appropriately operates the power supply unit ($D_1$ in FIG. 1) to supply required electric currents to the first and second deflectors 118A and 118B.

Figure 2D:
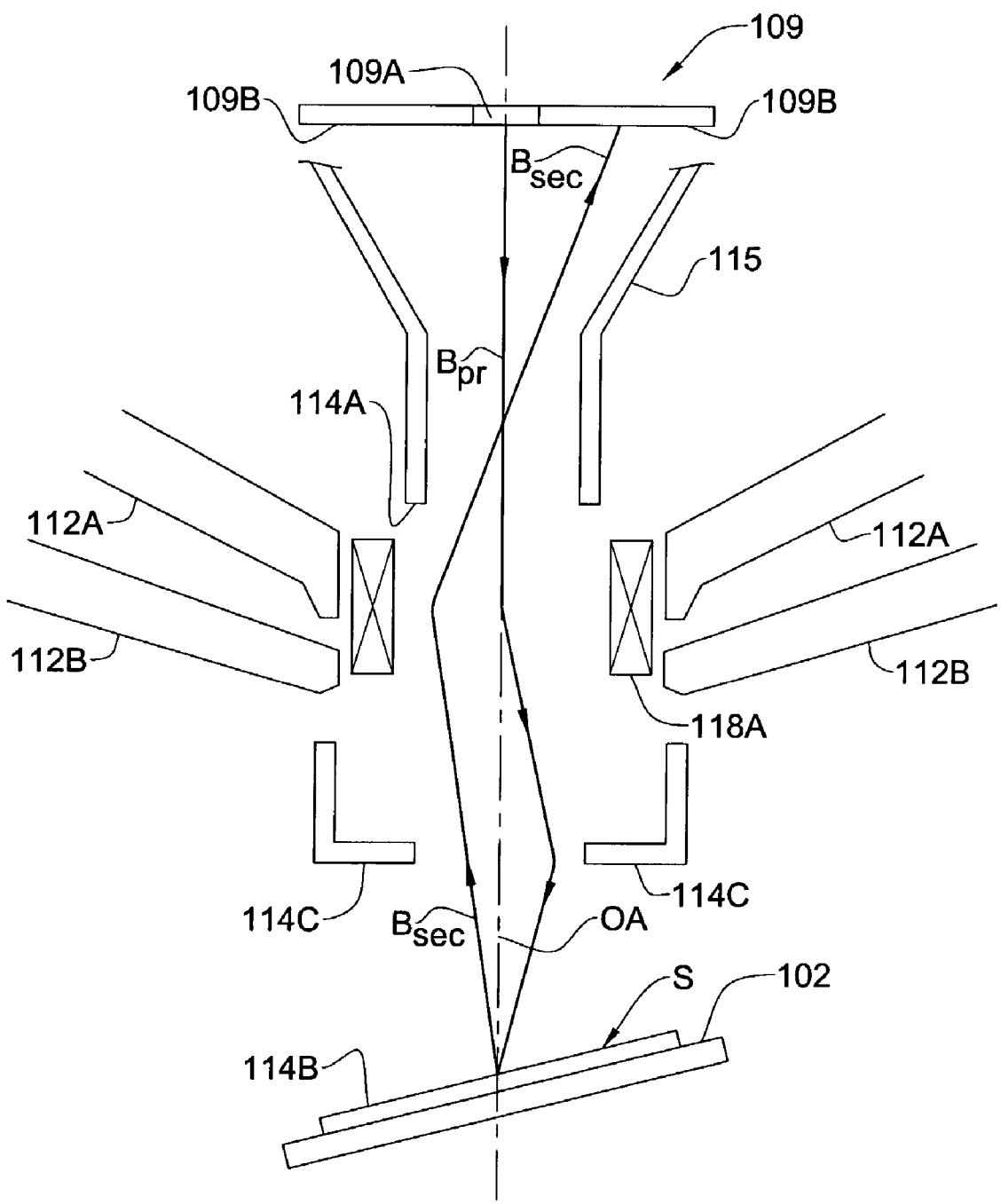

FIG. 2D illustrates yet another example of the implementation of the monitoring apparatus 100, namely, its beam directing arrangement. Here, in distinction to the previously described examples, the deflector arrangement comprises a single deflector 118A located in the magnetic lens gap. This may for example be a beam-shift deflector typically provided in the charged particle beam column. In this case, the deflector 118A affects the trajectory of the primary beam $B_{pr}$ to deflect it away from the optical axis OA and direct it along an axis $OA_1$ forming a certain angle with the optical axis OA. Then, the electric field, created by the lens arrangement (e.g., electrostatic lens) in the vicinity of the sample, further affects the trajectory of the beam $B_{pr}$ to deflect it in opposite direction, towards the optical axis OA. Secondary electrons $B_{sec}$ propagate perpendicular to the sample's surface and are then deflected by the deflector 118A to propagate towards the detecting regions of the detector. Using such a single deflector, while enabling less electronic tilt, might provide for better detection of the secondary electrons.

Figure 3:
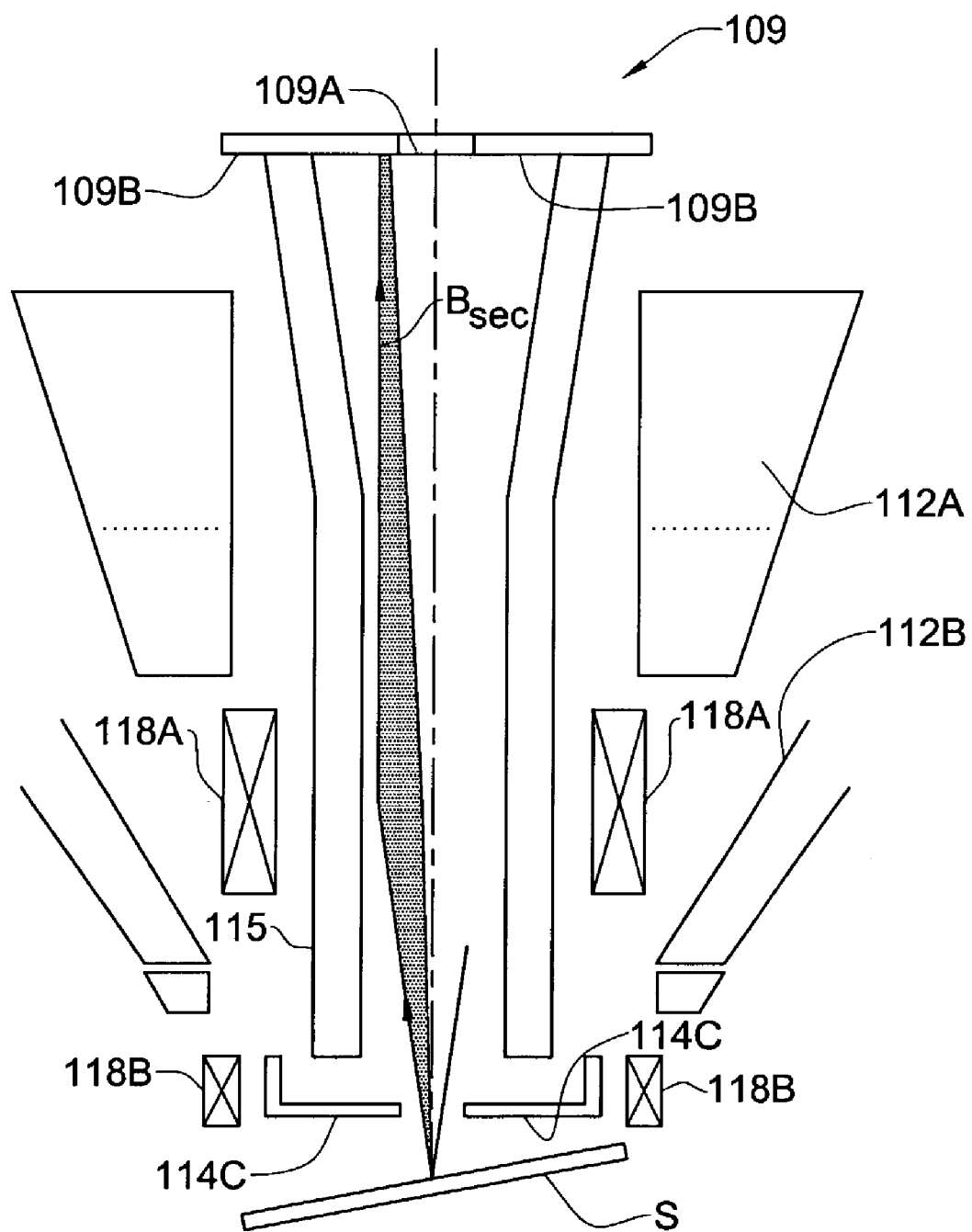
FIG. 3 shows the secondary electron beam propagation scheme in the apparatus of FIG. 1.

The deflection of the secondary electrons coming from the appropriately tilted sample's surface results in that the secondary beam $B_{sec}$ does not hit the funnel and substantially all the secondary electrons are sensed by the detecting region 109B (outside the primary beam hole). This is exemplified in FIG. 3 showing the secondary electron beam propagation scheme in the apparatus of FIG. 2A, resulting from the combined tilt of 25° formed by the mechanical tilt of 80° (10°-angle between the stage and the horizontal plane) and the electronic tilt of 15°. As shown, the 100% collection of the secondary electrons at the detecting regions 109B is provided.

Figure 4A:
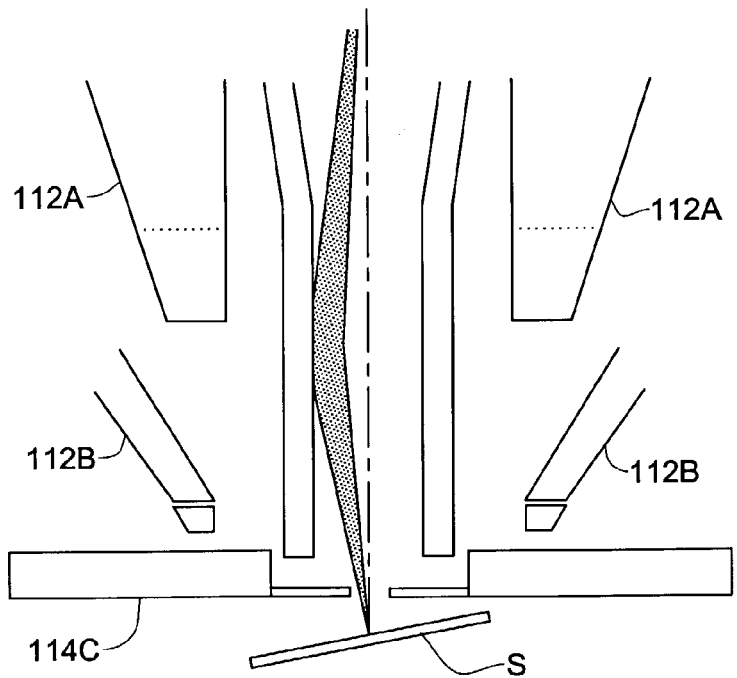
FIGS. 4A and 4B illustrate the secondary beam propagation schemes in the apparatus of FIG. 1, but operating with, respectively, the purely mechanical tilt and purely electronic tilt modes.
Figure 4B:
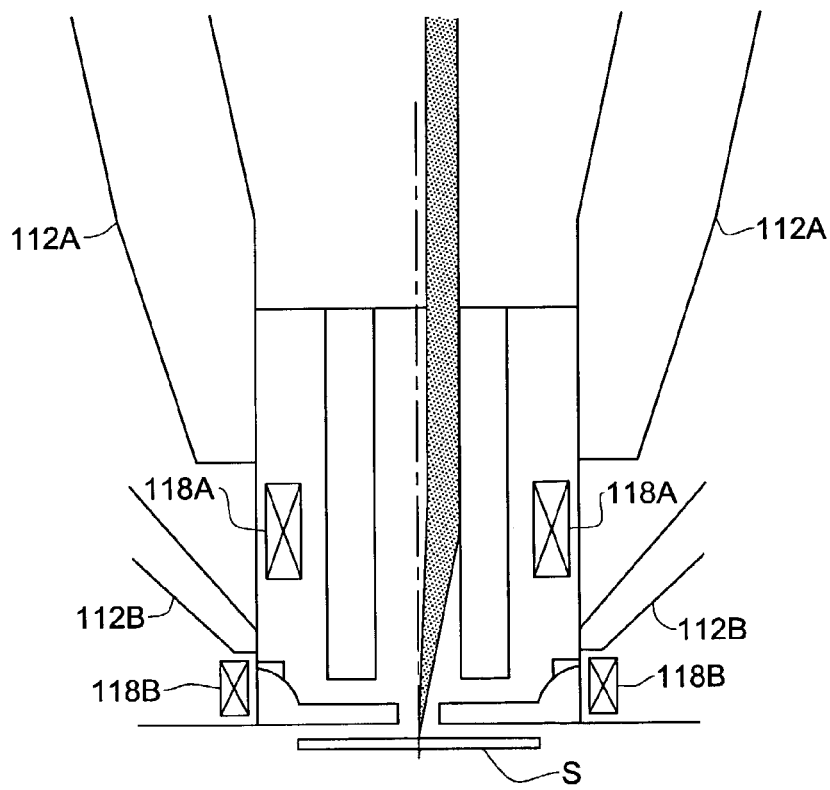

Reference is now made to FIGS. 4A and 4B showing the secondary beam propagation schemes in the apparatus of FIG. 1, but operating with, respectively, purely mechanical and purely electronic tilt. More specifically, the example of FIG. 4A corresponds to the in-operative state of the deflectors 118A and 118B and the 10° mechanical tilt (an angle between the plane defined by the stage and the horizontal plane, which means $\theta_2=80°$). As shown in FIG. 4A, a part of the secondary electron beam $B_{sec}$ hits the funnel, resulting in the electron collection loss at the detector. The example of FIG. 4B corresponds to the operative state of the deflectors 118A and 118B to provide an electronic tilt of 15° (angle $\theta_2$ between the primary beam propagation axis $OA_2$ and the optical axis OA), and the stage position perpendicular to the optical axis OA. Here again, about 10–15% of the secondary electrons hit the funnel. This effects is undesirable because of the secondary electron loss, and because this might cause charging of the funnel, and consequently, the image drift.

Images of the scan area on the sample obtained with the combined tilt technique of the present invention as compared to that obtainable with the purely electronic tilt (FIG. 5B) were taken. In these experiments the beam directing arrangement of FIG. 2A is used, the raster size (field of view) is 2 μm, and a 3 kV voltage is applied to the cup-electrode 114C. The purely electronic tilt of 15° (the stage is maintained perpendicular to the optical access with a working distance of 1 mm) is obtained by electric current supply of 0.62A and 0.308A to the deflectors 118A and 118B, respectively. The combined mechanical and electronic tilt of 19° (which is sufficiently high for the CD measurements) is obtained with a mechanical tilt of 10° ($\theta_2=80°$) resulting in a working distance of 2 mm, and an electronic tilt of 9° by the electric current supply of 0.25A and 0.1A to the deflectors 118A and 118B, respectively. Even with the higher working distance (as compared to that available with no mechanical tilt), the combined tilt technique of the present invention provides for a better image resolution.

It should be understood that the less the required combined tilt, the smaller electric current is needed to be supplied to the deflectors, thereby reducing the power and thermal effects. The image drift would thus be less.

It should also be understood that, with the mechanical tilt, the appropriate deflection of the primary electron beam to impinge onto the sample with a certain non-right angle $\theta_1$ between the beam propagation axis and the optical axis of the column can be aimed at providing the tilt mode (non-zero incidence of the primary beam), as well as the normal mode. It is often the case that monitoring of a sample requires selective switching from the normal mode to the tilt mode. Considering that monitoring of the topology of the sample's surface requires 10° and higher incident angles, such a switching would be easier to implement by the beam deflection while using the mechanical tilt (orienting the sample inclined with respect to the optical axis), namely, the changes in the current supply to the deflectors would be less, as compared to those required with the electronic tilt only to obtain the same beam incidence.

The technique of the present invention thus provides for obtaining a larger angle of primary beam incidence onto the sample (as compared to those obtainable with purely mechanical or purely electronic tilt) at sufficiently high image resolution and low power supply to the deflectors. Due to the fact that with the combined mechanical and electronic tilt a desirably high angle of incidence is obtained with a less component of electronic tilt, as compared to that of the purely electronic tilt, an energy spectrometric effect is less, and consequently, the physical and electric noise (e.g., beam vibration noise) is also reduced.

Those skilled in the art will readily appreciate that various modifications and changes can be applied to the embodiments of the invention as hereinbefore exemplified without departing from its scope defined in and by the appended claims.

The invention claimed is:

1. A method for use in monitoring a sample with a charged particle beam, the method comprising:
    tilting the sample with a certain non-right angle $\theta_1$ with respect to an optical axis defined by a beam directing arrangement of a charged particle beam column;
    deflecting a the primary charged particle beam produced by the charged particle beam column and propagating towards the sample so as to affect the trajectory of the primary charged particle beam to thereby form a certain non-zero angle $\theta_2$ between a primary beam propagation axis and said optical axis; and
    deflecting a trajectory of a secondary charged particle beam, which results from interaction of the primary charged particle beam with the sample, so as to direct substantially all particles in the secondary charged particle beam to a detector positioned within the charged particle beam column.

2. The method according to claim 1, wherein said tilting of the sample and said deflecting of the primary charged particle beam provides a desired angle of incidence of the primary charged particle beam onto the sample.

3. The method according to claim 1, wherein said tilting of the sample and said deflecting of the primary charged particle beam provides for controlling detection of secondary charged particles resulting from interaction of the primary charged particle beam with the sample.

4. The method according to claim 2, wherein said desired angle of incidence is about 10° and higher.

5. The method according to claim 4, wherein said desired angle of incidence is about 10°–25°.

6. The method according to claim 1, wherein said certain angle $\theta_1$ is provided by tilting the beam directing arrangement with respect to the sample.

7. The method according to claim 1, wherein deflecting the primary charged particle beam and the secondary charged particle beam creates a first and second deflection fields in spaced-apart regions along the optical axis.

8. The method according to claim 7, wherein said first and second deflection fields are created by first and second deflector units, respectively, of the beam directing arrangement.

9. The method according to claim 7, wherein said first and second deflection fields are created by, respectively, a field created by a deflector unit, and an electric field in a vicinity of the sample created by a lens arrangement.

10. The method according to claim 1, wherein said angles $\theta_1$ and $\theta_2$ are such that the primary charged particle beam impinges onto the sample along an axis substantially perpendicular to the sample's surface.

11. The method according to claim 1, wherein said angles $\theta_1$ and $\theta_2$ are such that the primary charged particle beam impinges onto the sample along an axis forming a certain non-zero angle with the normal to the sample's surface.

12. A method for use in monitoring a sample with a charged particle beam, the method comprising irradiating the sample with a primary charged particle beam impinging onto the sample with a desired angle of incidence, said irradiating with the desired angle of incidence comprising:

tilting the sample with a certain non-right angle $\theta_1$ with respect to an optical axis defined by a beam directing arrangement of a charged particle beam column;

deflecting the primary charged particle beam away from the optical axis to propagate along an axis forming a non-zero angle with the optical axis;

deflecting the primary charged particle beam propagating towards the optical axis and the sample to affect the trajectory of the primary charged particle beam to thereby form a certain non-zero angle $\theta_2$ between the primary beam propagation axis and said optical axis; and deflecting a secondary charged particle beam, which results from interaction of the primary charged particle beam with the sample, so as to direct substantially all charged particles in the secondary charged particle beam to a detector in the charged particle beam column.

13. A method for use in monitoring a sample with a charged particle beam, the method comprising controlling detection of secondary charged particles resulting from interaction of a primary charged particle beam with the sample, said controlling comprising:

providing a mechanical displacement between a plane defined by the sample's surface and an optical axis defined by a beam directing arrangement of a charged particle beam column, so as to tilt the sample with a certain non-right angle $\theta_1$ with respect to the optical axis;

deflecting the primary charged particle beam away from the optical axis to propagate along an axis forming an angle with the optical axis; and deflecting the primary charged particle beam from the axis forming an angle with the optical axis to thereby direct the primary charged particle beam towards the optical axis and onto the sample's surface with a certain non-zero angle $\theta_2$ between a propagation axis of the primary charged particle beam and said optical axis, and deflecting the secondary charged particle beam to direct particles thereof from the sample to a detector within the charged particle beam column along a path different from that of the primary charged particle beam.

14. An apparatus for use in monitoring a sample by a charged particle beam, the apparatus comprising:

a beam directing arrangement having a deflector arrangement operable to affect a trajectory of a primary charged particle beam to first direct the primary charged particle beam away from an optical axis and then to direct the primary charged particle beam towards the optical axis and the sample's surface with a certain non-zero angle $\theta_2$ between a propagation axis of the primary charged particle beam and the optical axis, and thereafter to deflect a secondary charged particle beam, resulting from interaction of the primary charged particle beam with the sample, to direct the secondary charged particle beam from the sample along a path different from that of the primary charged particle beam;

a detection unit having a detector located within a charged particle beam column and that has an opening and sensing regions outside said opening for sensing charged particles of the secondary charged particle beam, and is oriented with respect to the optical axis such that said optical axis passes through said opening, thereby enabling the primary charged particle beam's passage towards the sample through said opening;

a stage for handling the sample under inspection;

a drive assembly operable to provide a relative mechanical displacement between the stage and the beam directing arrangement to tilt the stage at a certain non-right angle $\theta_1$ with respect to the optical axis; and a control unit operating a power supply to said beam deflector arrangement and operating said drive assembly to provide desired values of said angles $\theta_1$ and $\theta_2$.

15. The apparatus according to claim 14, wherein said drive assembly comprises a drive mechanism associated with the stage to displace the stage with respect to the beam directing arrangement.

16. The apparatus according to claim 14, wherein said drive assembly comprises a drive mechanism associated with the beam directing arrangement to displace the beam directing arrangement with respect to the stage.

17. The apparatus according to claim 15, wherein said drive assembly comprises a drive mechanism associated with the beam directing arrangement to displace it with respect to the stage.

18. The apparatus according to claim 14, wherein the beam directing arrangement comprises a lens arrangement for creating a focusing field in the path of the primary charged particle beam.

19. The apparatus according to claim 18, wherein said lens arrangement is configured to create the focusing field acting as a retarding field for the primary charged particle beam in a vicinity of the sample's surface and acting as an accelerating field for the secondary charged particles beam.

20. The apparatus according to claim 18, wherein said lens arrangement comprises an objective magnetic lens.

21. The apparatus according to claim 18, wherein said lens arrangement comprises an objective magnetic lens creating a magnetic field, and an electrostatic lens creating an electric field in a vicinity of the sample's surface.

22. The apparatus according to claim 21, wherein said electrostatic lens comprises a cup electrode located between the objective magnetic lens and the sample's surface.

23. The apparatus according to claim 14, wherein said beam directing arrangements is configured to create at least two deflecting fields in two spaced-apart regions along the optical axis.

24. The apparatus according to claim 14, wherein said deflector arrangement comprises at least two deflector units located in spaced-apart regions along the optical axis.

25. The apparatus according to claim 24, wherein one of the deflector units is accommodated in a magnetic lens gap defined by an objective magnetic lens.

26. The apparatus according to claim 25, wherein at least one of the other deflector units is accommodated in a vicinity of the sample's surface downstream of a beam-shift deflector.

27. The apparatus according to claim 25, wherein at least one other of the deflector units is accommodated upstream of the objective magnetic lens.

28. The apparatus according to claim 24, wherein the deflector units are accommodated upstream of a lens arrangement.

29. The apparatus according to claim 23, wherein a first of the deflecting fields is created by a single deflector of the deflector arrangement accommodated in a magnetic lens gap defined by an objective magnetic lens, and a second of the deflection fields is an electric field created in a vicinity of the sample by an electrostatic lens.

30. An apparatus for use in monitoring a sample by a charged particle beam comprising:
- a beam directing arrangement having a deflector arrangement operable to affect a trajectory of a primary charged particle beam to first direct the primary charged particle beam away from an optical axis and then to direct the primary charged particle beam towards the optical axis and the sample's surface with a certain non-zero angle $\theta_2$ between a propagation axis of the primary charged particle beam and the optical axis, and further to affect a trajectory of a secondary charged particle beam, resulting from interaction of the primary charged particle beam with the sample, to direct the secondary charged particle beam from the sample along a path different from that of the primary charged particle beam;
- a detection unit having a detector located within a charged particle beam column and having an opening and sensing regions outside said opening for sensing the secondary charged particle beam, the detection being oriented with respect to the optical axis such that said optical axis passes through said opening, thereby enabling the primary charged particles beam passage towards the sample through said opening;
- a stage for handling the sample under inspection;
- a drive assembly operable to provide a relative mechanical displacement between the stage and the beam directing arrangement to thereby tilt the stage at a certain non-right angle $\theta_1$ with respect to the optical axis; and
- a control unit operating a power supply to said beam deflector arrangement and operating said drive assembly to provide desired values of said angles $\theta_1$ and $\theta_2$.

31. An apparatus for use in monitoring a sample by a charged particle beam, apparatus comprising:
- means for producing a primary charged particle beam and directing the primary charged particle beam first away from an optical axis and then to direct the primary charged particle beam towards the optical axis and a sample, to thereby cause interaction of the primary charged particle beam with the sample resulting in a secondary charged particle beam propagating from the sample;
- means for focusing the primary charged particle beam onto a scan area of the sample;
- beam deflecting means operable to affect a trajectory of the primary charged particle beam while being focused onto the sample so as to provide the primary charged particle beam incidence onto the scan area along an axis forming a certain non-zero angle $\theta_2$ with the optical axis, and to affect a trajectory of the secondary charged particle beam to direct the secondary charged particle beam along a path different from that of the primary charged particle beam to detector means located within a charged particle beam column which also houses the means for producing the primary charged particle beam;
- means for handling the sample on a substantially flat surface;
- driving means operable to provide a relative mechanical displacement between said flat surface and the means for focusing to thereby tilt said surface at a certain non-right angle $\theta_1$ with respect to the optical axis; and
- control means for operating said deflecting means and operating said driving means to provide desired values of said angles $\theta_1$ and $\theta_2$.

32. An apparatus for use in monitoring a sample by a charged particle beam, comprising:
- a charged particle beam column having a beam focusing arrangement defining an optical axis, and having a beam deflector arrangement operable to first direct a primary charged particle beam away from the optical axis and then to affect a trajectory of the primary charged particle beam to focus it towards the optical axis and onto the sample's surface with a certain non-zero angle $\theta_2$ between a propagation axis of the primary charged particle beam said optical axis, and to affect a trajectory of a secondary charged particle beam resulting from interaction of the primary charged particle beam with the sample, to direct the secondary charged particle beam from the sample along a path different from that of the primary charged particle beam to a detector located within the charged particle beam column;
- a stage for handling the sample under inspection;
- a drive assembly operable to provide a relative mechanical displacement between stage and the charged particle beam column to thereby create a certain non-right angle $\theta_1$ between the optical axis and a plane defined by the stage; and
- a control unit operating a power supply to said beam deflector arrangement and operating said drive assembly to provide desired values of said angles $\theta_1$ and $\theta_2$.

* * * * *